(12) United States Patent
Hayashi et al.

(10) Patent No.: US 10,604,889 B2
(45) Date of Patent: Mar. 31, 2020

(54) FIBROUS PRODUCT AND FIBER PROCESSING AGENT

(71) Applicant: HONDA MOTOR CO., LTD., Tokyo (JP)

(72) Inventors: Rie Hayashi, Wako (JP); Taro Suzuki, Osaka (JP); Kazuya Nishihara, Osaka (JP); Kohei Ohara, Echi-gun (JP); Yukihiko Shirahata, Echi-gun (JP); Eiken Kuzutani, Echi-gun (JP)

(73) Assignee: HONDA MOTOR CO., LTD., Tokyo (JP)

( * ) Notice: Subject to any disclaimer, the term of this patent is extended or adjusted under 35 U.S.C. 154(b) by 422 days.

(21) Appl. No.: 15/562,287

(22) PCT Filed: Jan. 18, 2016

(86) PCT No.: PCT/JP2016/051283
§ 371 (c)(1),
(2) Date: Sep. 27, 2017

(87) PCT Pub. No.: WO2016/157942
PCT Pub. Date: Oct. 6, 2016

(65) Prior Publication Data
US 2018/0051411 A1 Feb. 22, 2018

(30) Foreign Application Priority Data
Mar. 31, 2015 (JP) ................. 2015-070515

(51) Int. Cl.
*D06M 11/71* (2006.01)
*D06M 15/19* (2006.01)
*D06M 15/233* (2006.01)
*D06M 15/507* (2006.01)
*A01N 41/04* (2006.01)
*A01N 25/04* (2006.01)
*A01N 61/00* (2006.01)
*A01N 41/10* (2006.01)
*A01N 59/16* (2006.01)

(52) U.S. Cl.
CPC ............ *D06M 11/71* (2013.01); *A01N 25/04* (2013.01); *A01N 41/04* (2013.01); *A01N 41/10* (2013.01); *A01N 59/16* (2013.01); *A01N 61/00* (2013.01); *D06M 15/195* (2013.01); *D06M 15/233* (2013.01); *D06M 15/507* (2013.01); *D10B 2401/13* (2013.01)

(58) Field of Classification Search
CPC .. D06M 11/71; D06M 15/195; D06M 15/233; D06M 15/507; D06M 15/5075; D10B 2401/13; A01N 41/04; A01N 25/04; A01N 61/00; A01N 41/10; A01N 59/16
See application file for complete search history.

(56) References Cited

U.S. PATENT DOCUMENTS

| | | | |
|---|---|---|---|
| 2010/0209530 A1* | 8/2010 | Yamada | D60M 11/71 424/601 |
| 2011/0154791 A1* | 6/2011 | Fujiwara | D60M 15/233 442/59 |
| 2011/0269886 A1* | 11/2011 | Hayashi | D60M 11/71 524/376 |
| 2012/0093763 A1* | 4/2012 | Akamine | A61K 31/765 424/78.27 |
| 2015/0164070 A1 | 6/2015 | Akamine et al. | |

FOREIGN PATENT DOCUMENTS

| | | |
|---|---|---|
| JP | 2011-246859 A | 12/2011 |
| JP | 2011-246866 A | 12/2011 |
| JP | 2013-87386 A | 5/2013 |
| JP | 5215424 B2 | 6/2013 |
| JP | 5427219 B2 | 2/2014 |
| WO | 2013/146782 A1 | 10/2013 |

OTHER PUBLICATIONS

International Search Report dated Apr. 19, 2016, issued in counterpart International Application No. PCT/JP2016/051283 (1 page).

* cited by examiner

*Primary Examiner* — Jeremy R Pierce
(74) *Attorney, Agent, or Firm* — Westman, Hattori, Daniels & Adrian, LLP

(57) ABSTRACT

Provided is a fibrous product that has excellent anti-allergen and antiviral properties, is capable of maintaining excellent outer appearance, and is less likely to cause color migration. Also provided is a processing agent for producing the fibrous product. The fibrous product of the present invention is characterized in having attached to the surface thereof (a) 1.0 to 3.0 g/m² of zirconium phosphate, (b) 0.12 to 0.4 g/m² of a homopolymer formed of an aromatic sulfonic acid monomer, and (c) 0.2 to 0.8 g/m² of a copolymer including a styrene sulfonate salt. In addition, the processing agent of the present invention is characterized in being an aqueous dispersion that contains the components (a), (b), and (c) in a weight ratio of 1.0 to 3.0:0.12 to 0.4:0.2 to 0.8.

7 Claims, No Drawings

FIBROUS PRODUCT AND FIBER PROCESSING AGENT

TECHNICAL FIELD

The present invention relates to a functional fibrous product and a processing agent for producing the fibrous product. More specifically, the present invention relates to a fibrous product having an anti-allergen property and an antiviral property, and a processing agent for producing the fibrous product.

BACKGROUND ART

In recent years, with an increased interest in measures against allergy symptoms caused by pollen and mites and viral infectious diseases caused by, for example, an influenza virus, a demand is increasing for a functional fibrous product having an anti-allergen property and an antiviral property in a field of fibrous products.

Under the circumstances, for example, Patent Document 1 discloses, as a fibrous fabric having an antibacterial, antiviral, and anti-allergen function, a fibrous fabric to which are fixed, with a binder resin, an inorganic antibacterial and antiviral agent, an allergen adsorbent formed of an inorganic layered mineral, and a chelate complex.

In Patent Document 1, however, the antiviral property is evaluated 24 hours after virus inoculation, and those having a virus removal efficiency of 80% or more are determined to be acceptable. In contrast, in an antiviral property test according to ISO18184 (Textiles-Determination of antiviral activity of textile products) issued in September, 2014, the antiviral property is determined 2 hours after virus inoculation, so that a higher performance fibrous product is required that can exhibit sufficient antiviral action within 2 hours (for example, a fibrous product exhibiting a virus removal efficiency of 99.9% or more (antiviral activity value of 3 or more) in a test at 25° C. after 2 hours that is specified in the ISO or a test at a lower temperature after a shorter period).

The applicants of the present application have so far filed applications of inventions related to Patent Documents 2 and 3 for the purpose of providing an anti-allergen fibrous product. The fibrous product disclosed in Patent Document 2 has been confirmed to maintain, in addition to the anti-allergen property, excellent outer appearance (less likely to generate water spots, whitening, and chalk marks). The product disclosed in Patent Document 3 has been confirmed to be excellent also in fastness to rubbing. These fibrous products, however, do not have an antiviral property. Further, a problem has been confirmed that chalk marks are likely to be generated or fastness to rubbing is decreased in a fibrous product treated with an agent obtained by adding an antiviral agent to an allergen reduction-processing agent that is actually used in Patent Documents 2 and 3.

PRIOR ART DOCUMENTS

Patent Documents

Patent Document 1: JP-A-2011-246859
Patent Document 2: JP 5215424 B2
Patent Document 3: JP 5427219 B2

SUMMARY OF THE INVENTION

Problems to be Solved by the Invention

An object of the present invention is to solve the problems described above, to provide a fibrous product that has excellent anti-allergen and antiviral properties, is capable of maintaining excellent outer appearance (less likely to generate whitening, chalk marks, and water spots), and is less likely to cause color migration (high in fastness to rubbing), and to provide a processing agent for producing the fibrous product.

Means for Solving the Problems

The present inventors have succeeded in applying the anti-allergen property and the antiviral property to a fibrous product while suppressing whitening, chalk marks, water spots, and color migration, by fixing, with a binder, two specific anti-allergen agents (zirconium phosphate and a homopolymer formed of an aromatic sulfonic acid monomer) and a specific antiviral agent (a copolymer including a styrene sulfonate salt) to the fibrous product in a specific ratio.

That is, a fibrous product of the present invention is characterized in having attached thereto
(a) 1.0 to 3.0 g/m$^2$ of zirconium phosphate;
(b) 0.12 to 0.4 g/m$^2$ of a homopolymer formed of an aromatic sulfonic acid monomer; and
(c) 0.2 to 0.8 g/m$^2$ of a copolymer including a styrene sulfonate salt.

In the present invention, two specific anti-allergen agents (zirconium phosphate and a homopolymer formed of an aromatic sulfonic acid monomer) are used in combination, a specific antiviral agent (a copolymer including a styrene sulfonate salt) is further used, and these agents are attached to a fibrous product in a specific ratio, so that a fibrous product can be provided that has high anti-allergen and antiviral properties, is less likely to generate whitening, chalk marks, and water spots, and in high in fastness to rubbing.

Particularly, an attachment amount of the zirconium phosphate (a) is preferably 1.5 to 2.5 g/m$^2$, an attachment amount of the homopolymer (b) formed of an aromatic sulfonic acid monomer is preferably 0.18 to 0.36 g/m$^2$, and an attachment amount of the copolymer (c) including a styrene sulfonate salt is preferably 0.3 to 0.7 g/m$^2$.

The attachment amount of the zirconium phosphate (a) is further preferably 2.0 to 2.5 g/m$^2$, the attachment amount of the homopolymer (b) formed of an aromatic sulfonic acid monomer is further preferably 0.24 to 0.3 g/m$^2$, and the attachment amount of the copolymer (c) including a styrene sulfonate salt is further preferably 0.35 to 0.5 g/m$^2$.

The components (a) to (c) are attached to the fibrous product with a binder, and an attachment amount of the binder is preferably 0.05 to 1.5 g/m$^2$.

Preferable examples of the binder include a polyester resin.

In addition, the present invention relates to an aqueous dispersion that is a processing agent for producing the fibrous product and contains the zirconium phosphate (a), the homopolymer (b) formed of an aromatic sulfonic acid monomer, and the copolymer (c) including a styrene sulfonate salt in a weight ratio of 1.0 to 3.0:0.12 to 0.4:0.2 to 0.8.

Effect of the Invention

According to the present invention, there can be provided a fibrous product that has anti-allergen and antiviral properties, is less likely to generate whitening, water spots, chalk marks and so on, and is high in fastness to rubbing.

MODE FOR CARRYING OUT THE INVENTION

To a fibrous product according to the present invention are attached two anti-allergen agents having an effect (anti-allergen property) of inactivating allergens attributed to pollen and mites.

One of the anti-allergen agents is zirconium phosphate (a). Particularly, layered zirconium phosphate is preferable that has a crystalline layered structure. As the zirconium phosphate (a), there can be used, for example, AlleRemove (registered trade name) ZK-200 commercially available from TOAGOSEI CO., LTD. The attachment amount of the zirconium phosphate (a) to the fibrous product is appropriately 1.0 to 3.0 g/m$^2$. An attachment amount of less than 1.0 g/m$^2$ may possibly make the anti-allergen property insufficient, and an attachment amount of more than 3.0 g/m$^2$ makes the fibrous product likely to generate chalk marks. The attachment amount of the zirconium phosphate is more preferably 1.5 to 2.5 g/m$^2$, particularly preferably 2.0 to 2.5 g/m$^2$.

Another anti-allergen agent used in the present invention is a homopolymer (b) formed of an aromatic sulfonic acid monomer (an aromatic compound having a sulfonic acid group and a polymerizable functional group). In the homopolymer, the sulfonic acid group is particularly preferably present in a form of a sodium salt (—SO$_3$Na). The homopolymer (b) having a low weight average molecular weight sometimes decreases the anti-allergen effect, and therefore the homopolymer preferably has a weight average molecular weight of 200,000 or more. On the other hand, the homopolymer (b) having a weight average molecular weight of more than 2,000,000 may possibly cause a failure such as hardening of the fibrous product. Therefore, the homopolymer (b) of the present invention preferably has a weight average molecular weight ranging from 200,000 to 2,000,000. As the homopolymer (b) of the present invention, there can be used, for example, SSPA-FB which is commercially offered from SEKISUI POLYMATECH CO., LTD, as an anti-allergy agent. The attachment amount of the homopolymer (b) of the present invention to the fibrous product is appropriately 0.12 to 0.4 g/m$^2$. An attachment amount of less than 0.12 g/m$^2$ may possibly make the anti-allergen property insufficient, and an attachment amount of more than 0.4 g/m$^2$ makes the fibrous product likely to generate chalk marks. The attachment amount is more preferably 0.18 to 0.36 g/m$^2$, particularly preferably 0.24 to 0.3 g/m$^2$.

In the present invention, a copolymer (c) including a styrene sulfonate salt is also used as an antiviral agent for performing antiviral processing on the fibrous product. An influenza virus binds with a sugar chain receptor (the terminal of the sugar chain is neuraminic acid) on the surface of a host cell to enter into the host cell, whereas it is considered that the copolymer including a styrene sulfonate salt has an ionic group similar to neuraminic acid, binding with the virus in place of the host cell to catch the virus and thus preventing the virus from binding with the receptor of the host cell to exhibit an antiviral effect. The styrene sulfonate salt is essential in order to make the copolymer exhibit the antiviral effect, and it exhibits a higher antiviral effect when forming a copolymer with other polymerizable monomer(s) in comparison to when being a homopolymer of itself. Therefore, in the present invention, the copolymer (c) formed of a styrene sulfonate salt and other polymerizable monomer(s) is used as the antiviral agent. The other polymerizable monomer is not particularly limited, and examples thereof include alkyl acrylate, alkyl methacrylate, vinyl alkyl ether, vinyl acetate, ethylene, propylene, butylene, butadiene, diisobutylene, vinyl chloride, vinylidene chloride, 2-vinylnaphthalene, styrene, acrylonitrile, acrylic acid, sodium acrylate, methacrylic acid, maleic acid, fumaric acid, maleic anhydride, acrylamide, methacrylamide, diacetone acrylamide, vinyl toluene, xylenesulfonic acid, vinylpyridine, vinyl sulfonic acid, vinyl alcohol, methyl methacrylate, sodium methacrylate, hydroxyethyl methacrylate, and 2-vinylnaphthalene. Styrene and 2-vinylnaphthalene are more preferable, and styrene is particularly preferable. As the copolymer (c) of the present invention, there can be used, for example, Infebuster (registered trade name) FH commercially available from SEKISUI POLYMATECH CO., LTD, as an antiviral processing agent. The attachment amount of the copolymer (c) of the present invention to the fibrous product is appropriately 0.2 to 0.8 g/m$^2$. An attachment amount of less than 0.2 g/m$^2$ may possibly make the antiviral property insufficient, and an attachment amount of more than 0.8 g/m$^2$ may possible make the fastness to rubbing insufficient. The attachment amount is particularly preferably 0.3 to 0.7 g/m$^2$, further preferably 0.35 to 0.50 g/m$^2$.

In the present invention, a binder can also be used to attach (fix) the anti-allergen agents and the antiviral agent to the fibrous product. As the binder, there can be used, for example, a polyester resin, an acrylic resin, and a urethane resin. The binder also plays a role in an increase of resistance to abrasion of the fibrous product, so that the use of the binder can provide a fibrous product suitable for application (e.g., vehicle sheets) that requires toughness against abrasion.

As the polyester resin, there can be preferably used particularly a water-soluble or water-dispersible polyester resin, for example, a polyester resin containing in its molecule a hydrophilic component such as polyethylene glycol, a carboxyl group, a carbonyl group, a carboxylate salt, a sulfonate salt, a sulfate ester salt, or a phosphate ester salt.

As the acrylic resin, any normal processing resin can be used, and a resin including 70% or more of butyl acrylate and/or ethyl acrylate is particularly preferable from the viewpoint of flexibility of the fibrous product when the resin is fixed to the surface thereof. Further, the acrylic resin preferably includes, as a cross-linkable monomer, 1 to 10% e of an acrylic monomer (e.g., n-butoxymethylolacrylamide, glycidyl methacrylate, diacetone acrylate acrylamide, and n-methylolacrylamide) having a functional group such as an epoxide group, an amino group, a carboxyl group, a hydroxyl group, or an amide group, in view of film strength of the acrylic resin. The percent (%) is based on the component ratio of monomers that constitute the acrylic resin.

Particularly, the acrylic resin preferably has a glass-transition point of −45° C. to −5° C. This is because the acrylic resin having such a glass-transition point can allow the fibrous product to retain flexibility when the acrylic resin is fixed to the surface of the fibrous product. The glass-transition point can be measured by differential scanning calorimetry (DSC).

The attachment amount of the binder to the fibrous product is appropriately 0.05 to 1.5 g/m$^2$. An excessively small attachment amount of the binder makes it difficult to sufficiently fix the anti-allergen agents and the antiviral agent to the fibrous product, and an excessively large attachment amount of the binder may possibly decrease the resistance to abrasion.

For example, for a fabric required of flame resistance, such as an interior fabric for a vehicle and an airplane, or a fabric used as a curtain, the polyester resin is preferably used as the binder. When the binder is the polyester resin, the attachment amount to the fibrous product is more preferably 0.5 to 1.5 g/m², particularly preferably 0.66 to 1.32 g/m², further preferably 0.88 to 1.1 g/m².

On the other hand, for a fabric required of no color migration even when rubbed with clothes of a person, such as a fabric used for a chair and a sofa, a small amount of the binder is preferable, so that it is preferable to use as the binder the acrylic resin that is high in adhesion force and is capable of fixing the antiviral agent and the anti-allergen agents to the fibrous product even in a small amount. When the binder is the acrylic resin, the binder can sufficiently fix the anti-allergen agents and the antiviral agent to the fibrous product even when the attachment amount of the binder is decreased to about 0.05 to 0.25 g/m².

The zirconium phosphate is preferably present in particulate form and is preferably present in the form of particles having an average particle size of 0.3 to 2.0 μm, for example. The particles having an average particle size of less than 0.3 μm are likely to cause recondensation, making it difficult to prepare a stable paste or dispersion liquid, and the particles having an average particle size of more than 2.0 μm may possibly make suppression of whitening insufficient. The average particle size can be measured by using a scattering particle size distribution analyzer (e.g., the scattering particle size distribution analyzer LA-950 [manufactured by HORIBA, Ltd.]).

In order to attach the anti-allergen agents and the antiviral agent to the fibrous product, it is preferable to prepare a processing agent formed of an aqueous dispersion (an aqueous paste or aqueous dispersion liquid) containing the anti-allergen agents, the antiviral agent, and the binder, and treat the fibrous product with the processing agent.

In the processing agent (aqueous dispersion), the mixing ratio by weight among the zirconium phosphate (a), the homopolymer (b) formed of an aromatic sulfonic acid monomer, and the copolymer (c) including a styrene sulfonate salt is preferably 1.0 to 3.0:0.12 to 0.4:0.2 to 0.8, more preferably 1.5 to 2.5:0.18 to 0.36:0.3 to 0.7, particularly preferably 2.0 to 2.5:0.24 to 0.3:0.35 to 0.5.

In processing the fibrous product with the processing agent of the present invention, the processing agent may be applied, by a method such as padding, dipping, or coating, to the fibrous product, which is then heated for drying. In a case of a dipping treatment, the total percent by weight of the anti-allergy agents and the antiviral agent in the processing agent is preferably 0.4 to 5.5% by weight, more preferably 1 to 5% by weight, particularly preferably about 1.3 to 4% by weight. This concentration is a concentration (final concentration) for actually performing the treatment. The processing agent according to the present invention may be produced in a condensed state and diluted for use to the concentration described above at the time of use. For example, a condensed liquid at a concentration of about 2 to 70 times can be produced and diluted for use with water to about 2 to 70 times at the time of use.

After the processing agent of the present invention is applied to the fibrous product (for example, after performing the dipping treatment on the fabric), it is preferable to dry the fibrous product at 120 to 170° C. Drying at 170° C. or less, particularly 150° C. or less can effectively prevent a decrease in performance of the fastness to rubbing and further impart a very excellent effect of both an anti-mite-allergen property and an anti-pollen-allergen property.

As the fibrous product of the present invention, there can be used a fabric (e.g., a woven fabric, a knitted fabric, felt, and a nonwoven fabric) made of one or two or more fibers selected from a natural fiber (cotton, hemp, wool, silk, etc.), a regenerated fiber (rayon, etc.), a semisynthetic fiber (acetate, etc.), and a synthetic fiber (polyester-based, polyamide-based, or polyacrylonitrile-based). Particularly, a fabric made of a polyester fiber is preferable.

Next, the present invention is described in further detail with reference to comparative examples and examples. The present invention, however, is not to be limited to the examples.

EXAMPLES

Example 1

Water dispersions (processing agents) were produced that contained anti-allergen agents and an antiviral agent in various ratios as shown in Tables 1a to 1c. The anti-allergen agents, the antiviral agent, and the binders that were used in the examples are as follows.

Anti-allergen agents

α-zirconium phosphate: AlleRemove ZK-200 (TOAGOSEI CO., LTD.)

Homopolymer formed of aromatic sulfonic acid monomer SSPA-FB (SEKISUI POLYMATECH CO. LTD.)

Antiviral agent

Copolymer including styrene sulfonate salt: Infebuster FH, product number; SSPI-FH (SEKISUI POLYMATECH CO., LTD.)

Binder

Polyester resin: PLAS-COAT Z (GOO CHEMICAL CO., LTD.)

Acrylic resin: Newcoat FH (Shin Nakamura Chemical Co., Ltd.)

A polyester knit (polyester 100%, A3 size, weight 360 g/m²) that had been dyed in black with a disperse dye was immersed in the processing agent, next squeezed (squeeze rate 65%) with mangles at a roll pressure of 3.0 kgf/cm², and dried at 130° C. for 2 minutes and 30 seconds.

The processed polyester knit (hereinafter, referred to as a processed fabric) was measured for its anti-mite-allergen property, anti-cedar-pollen-allergen property, antiviral property, water spots, whitening, chalk marks, fastness to rubbing, and flame resistance. Tables 1a to 1c show the results.

In Tables 1a to 1c, the values of the anti-allergen agents, the antiviral agent, and the binders show the attachment amount per 1 m² (g/m²) of the processed fabric in a solid content. As the processing agent (water dispersion), used was a processing agent having a concentration that was converted from the attachment amount, on the basis of attachment amount 1 g/m²=0.426% by weight.

Performance evaluation methods of the fibrous product are as follows.

<Anti-allergen Property (Mite)>

The processed fabric at a size of 5 cm×2.5 cm was placed in a test tube, thereto was dropwise added 2.25 ml of a solution containing 47 ng/ml of a mite allergen, and the processed fabric was cured at 37° C. for 8 hours. The amount of the allergen in the solution is measured by the Enzyme-Linked Immuno Sorbent Assay (ELISA), and an inactivity rate is calculated by the following equation. The amount of the mite allergen denotes the total amount of protein converted from the amount of Derf II.

Inactivity rate=[(amount of allergen charged−amount of allergen measured after curing)×100]/amount of allergen charged The processed fabric having an allergen inactivity rate (anti-allergen property) of 90% or more is determined to be acceptable.

<Anti-allergen Property (Cedar)>

The processed fabric at a size of 5 cm×2.5 cm was placed in a test tube, thereto was dropwise added 2.25 ml of a solution containing 6.7 ng/ml of a cedar allergen, and the processed fabric was cured at 20° C. for 24 hours. The amount of the allergen in the solution is measured by ELISA, and an inactivity rate is calculated by the following equation. The amount of the cedar pollen allergen denotes the total amount of protein converted from the amount of Cryj I.

Inactivity rate=[(amount of allergen charged−amount of allergen measured after curing)×100]/amount of allergen charged The processed fabric having an inactivity rate (anti-allergen property) of 70% or more is determined to be acceptable.

<Antiviral Property (25° C. for 2 Hours)>
1. Prepared is a virus suspension (influenza virus A [mouse H1N1] suspension).
2. To the processed fabric (0.4 g) cut at 3-cm square is dropwise added 0.2 mL of the virus suspension, and the processed fabric is left to stand at 25° C. for 2 hours.
3. Thereafter, the processed fabric is placed in a centrifuge tube, to which 1.8 ml of a maintenance medium is added, and centrifugalized to extract 1 ml of a reaction liquid.
4. The extracted reaction liquid is diluted with a maintenance medium to prepare dilution series (10 times, 100 times, 1,000 times, 10,000 times, and 100,000 times).
5. Host cells (MDBK cells: derived from bovine kidney cells) are inoculated with the dilution series, and a dilution rate at which 50% of the cells are infected ($TCID_{50}$: Median tissue culture infectious dose) is acquired (this value is defined as a virus infectivity titer $V_c$).
6. With the virus infectivity titer of an unprocessed fabric defined as $V_b$, a virus reduction rate is acquired by the following equation I.

Virus reduction rate (%)=[($V_b$−$V_c$)×100]/$V_b$     Equation I:

Further, an antiviral activity value (Mv) is acquired by the following equation II.

$Mv=lg_{10}(V_b)-lg_{10}(V_c)$     Equation II:

Tables 1a to 1c show the virus reduction rate and the antiviral activity value that is indicated in parentheses.

The processed fabric having a virus reduction rate of 99.9% or more (an antiviral activity value of 3 or more) is determined to be acceptable.

<Antiviral Property (4° C. for 15 Minutes)>

With an ambient temperature in winter simulated and for confirmation of whether or not the antiviral property can be obtained in a shorter period, a test was performed by changing the conditions for leaving the processed fabric to stand in the procedure "2" from at 25° C. for 2 hours to at 4° C. for 15 minutes. The other procedures are as mentioned above.

The processed fabric having a virus reduction rate of 99.9% or more (an antiviral activity value of 3 or more) is determined to be acceptable.

<Water Spots>

The presence or absence of water spots (color change) was confirmed and a grade was determined according to the following criteria, for the processed fabric that had dropwise added to the surface thereof 5 ml of purified water and was naturally dried for 24 hours (I), and for the processed fabric at the initial period and 3 minutes after the processed fabric had dropwise added to the surface thereof 5 ml of hot water at 95° C. (II). In the water spot test, white water spots were confirmed with black processed fabrics produced in the method described above, and black water spots were also confirmed with beige processed fabrics. The beige processed fabrics were produced in the method of producing a processed fabric described above except that a polyester knit dyed to beige was used in place of the polyester knit dyed with a black disperse dye. In both the water (I) and hot water (II) tests performed with both the black and beige processed fabrics, it is confirmed whether or not the following determination criteria are satisfied, and the processed fabric at the 3rd grade or higher is determined to be acceptable.

| Determination | Criteria |
| --- | --- |
| 5th grade | No color change |
| 4th grade | Change of color almost not recognized |
| 3rd grade | Change of color slightly recognized |
| 2nd grade | Change of color easily recognized |
| 1st grade | Significant change of color |

<Whitening>

The processed fabric was confirmed for its change in color (whitening) in comparison with a fabric before processing (unprocessed fabric) and a grade was determined according to the following criteria. The fabric at the 3rd grade or higher is determined to be acceptable.

| Determination | Criteria |
| --- | --- |
| 5th grade | No color change |
| 4th grade | Change of color almost not recognized |
| 3rd grade | Change of color slightly recognized |
| 2nd grade | Change of color easily recognized |
| 1st grade | Significant change of color |

<Chalk Marks>

In order to confirm whether chalk marks (whitening caused by scratches) in the processed fabric were deteriorated in comparison with in an unprocessed fabric, the surfaces of the processed fabric and the unprocessed fabric were lightly rubbed with a nail and compared in terms of the degree of whitening caused by scratches, and a grade was determined according to the following criteria. The fabric at the 3rd grade or higher is determined to be acceptable.

| Determination | Criteria |
| --- | --- |
| 5th grade | No color change |
| 4th grade | Change of color almost not recognized |
| 3rd grade | Change of color slightly recognized |
| 2nd grade | Change of color easily recognized |
| 1st grade | Significant change of color |

<Fastness to Rubbing>

The processed fabric was subjected to a dry test (DRY) and a wet test (WET) in accordance with JIS L0849 (TEST METHODS FOR COLOR FASTNESS TO RUBBING). The determination of staining was performed with a gray scale for assessing staining (JIS L0805), and a grade was determined from the 1st to 5th grades. The processed fabric at the 3.5th grade (between the 3rd grade and the 4th grade) or higher is determined to be acceptable.

<Flame Resistance Performance>

A test was performed in accordance with "Flammability of Interior Materials" specified in the Federal Motor-Vehicle Safety Standard (FMVSS), and flame resistance performance was determined.

The term "flame resistance" indicates that the processed fabric was not ignited even to which flame was applied for 15 seconds.

A term "self-extinguishing" indicates that flame was extinguished within a burning distance of 50 mm and a burning period of 60 seconds after the flame was beyond a marked line A. For the processed fabric that did not satisfy the criteria "flame resistance" and "self-extinguishing," a burning speed (mm/min) is listed in the tables.

Total Evaluation

The processed fabric was evaluated as a good product (circle) when satisfying all the conditions of an anti-mite-allergen property of 90% or more, an anti-cedar-pollen-allergen property of 70% or more, an antiviral property of 99.9% or more (an antiviral activity value of 3 or more) at the test at 25° C. for 2 hours and/or the test at 4° C. for 15 minutes, the 3rd grade or higher in each of the water spots, the whitening, and the chalk marks, the 4th grade or higher of the fastness to rubbing in the dry test, and the 3.5th grade or higher of the fastness to rubbing in the wet test. Especially, the processed fabric that exhibited particularly excellent performance (specifically, the processed fabric satisfying an anti-mite-allergen property of 91% or more, an anti-cedar-pollen-allergen property of 90% or more, an antiviral property of 99.9% or more in the test at 4° C. for 15 minutes, and the 4th grade or higher of the fastness to rubbing in the wet test) was evaluated as an excellent product (double circle). As to No. 11, because the amount of the antiviral agent was the same as in No. 10, assuming that the criterion of the antiviral property was cleared, the total evaluation was performed. As to Nos. 16 to 18, because the amounts of the anti-allergen agents were the same as in No. 15, assuming that the criteria of the anti-allergen properties were cleared, the total evaluation was performed.

The processed fabric that did not satisfy one or more criteria for the good product was evaluated as unacceptable (cross mark), and some processed fabrics were not subjected to the antiviral property test when proved to be unacceptable.

TABLE 1a

|  |  | No. 1 | No. 2 | No. 3 | No. 4 | No. 5 | No. 6 | No. 7 | No. 8 |
|---|---|---|---|---|---|---|---|---|---|
| Attachment amount (g/m$^2$) | Anti-allergen agent A (component a) *$^1$ | 0 | 4.5 | 4.5 | 4.5 | 3.5 | 2.5 | 1.5 | 1.0 |
|  | Anti-allergen agent B (component b) *$^2$ | 0 | 0.5 | 0.5 | 0.5 | 0.5 | 0.5 | 0.5 | 0.5 |
|  | Antiviral agent (component c) *$^3$ | 0 | 0 | 0.5 | 0.5 | 0.5 | 0.5 | 0.5 | 0.5 |
|  | Acrylic resin | 0 | 0 | 0 | 1.1 | 0 | 0 | 0 | 0 |
|  | Polyester resin | 0 | 1.1 | 1.1 | 0 | 1.1 | 1.1 | 1.1 | 1.1 |
| Anti-allergen property (mite) |  | — | 93.8% | 93.8% | 93.8% | 93.8% | 93.8% | 93.8% | 93.8% |
| Anti-allergen property (cedar pollen) |  | — | 96.1% | 97.6% | 97.6% | 97.3% | 94.8% | 97.6% | 97.6% |
| Antiviral property (25° C. for 2 hours) |  | — | — | — | — | — | — | — | — |
| Antiviral property (4° C. for 15 minutes) |  | — | 39.8% (0.2) | — | — | — | — | — | — |
| Water spots (grade) |  | 5 | 4 | 4 | 4 | 4 | 4 | 4 | 4 |
| Whitening (grade) |  | 5 | 4 | 4 | 4 | 4 | 4 | 4 | 4 |
| Chalk marks (grade) |  | 5 | 3 | 2 | 2 | 2 | 4 | 4 | 4 |
| Fastness to rubbing DRY (grade) |  | 4.5 | — | 4.0 | 4.0 | 4.0 | 4.0 | 4.0 | 4.0 |
| Fastness to rubbing WET (grade) |  | 4.5 | — | 3.0 | 3.5 | 3.0 | 3.0 | 3.0 | 3.0 |
| Flame resistance performance |  | Flame resistance | Flame resistance | Self-extinguishing | 102 (mm/min) | Flame resistance | Flame resistance | Self-extinguishing | Flame resistance |
| Total Evaluation |  | X | X | X | X | X | X | X | X |

*$^1$ Zirconium phosphate
*$^2$ Homopolymer formed of aromatic sulfonic acid monomer
*$^3$ Copolymer including styrene sulfonate salt TABLE 1b

|  |  | No. 9 | No. 10 | No. 11 | No. 12 | No. 13 | No. 14 | No. 15 | No. 16 |
|---|---|---|---|---|---|---|---|---|---|
| Attachment amount (g/m$^2$) | Anti-allergen agent A (component a) *$^1$ | 2.5 | 2.5 | 2.5 | 2.5 | 2.5 | 2.5 | 2.5 | 2.5 |
|  | Anti-allergen agent B (component b) *$^2$ | 0.7 | 0.3 | 0.2 | 0.1 | 0.3 | 0.3 | 0.3 | 0.3 |
|  | Antiviral agent (component c) *$^3$ | 0.5 | 0.5 | 0.5 | 0.5 | 0.35 | 0.4 | 0.45 | 0.55 |
|  | Acrylic resin | 0 | 0 | 0 | 0 | 0 | 0 | 0 | 0 |
|  | Polyester resin | 1.1 | 1.1 | 1.1 | 1.1 | 1.1 | 1.1 | 1.1 | 1.1 |
| Anti-allergen property (mite) |  | 93.8% | 93.8% | 90.4% | 88.0% | 95.6% | 95.5% | 95.4% | — |
| Anti-allergen property (cedar pollen) |  | 93.5% | 97.6% | 72.8% | 66.0% | 95.3% | 95.3% | 95.3% | — |
| Antiviral property (25° C. for 2 hours) |  | — | 99.9% (3.0) | — | — | — | — | — | — |
| Antiviral property (4° C. for 15 minutes) |  | — | 99.99% (4.0) | — | — | 99.99% (4.0) | 99.99% (4.0) | 99.99% (4.0) | 99.99% (4.0) |

TABLE 1b-continued

|  | No. 9 | No. 10 | No. 11 | No. 12 | No. 13 | No. 14 | No. 15 | No. 16 |
|---|---|---|---|---|---|---|---|---|
| Water spots (grade) | 4 | 4 | 4 | 4 | 4 | 4 | 4 | 4 |
| Whitening (grade) | 4 | 4 | 4 | 4 | 4 | 4 | 4 | 4 |
| Chalk marks (grade) | 4 | 4 | 4 | 4 | 4 | 4 | 4 | 4 |
| Fastness to rubbing DRY (grade) | 4.0 | 4.0 | 4.0 | 4.0 | 4.0 | 4.0 | 4.0 | 4.0 |
| Fastness to rubbing WET (grade) | 2.5 | 4.0 | 4.0 | 4.0 | 4.0 | 4.0 | 4.0 | 3.5 |
| Flame resistance performance | Self-extinguishing | Flame resistance | Flame resistance | Flame resistance | Flame resistance | Flame resistance | Self-extinguishing | Flame resistance |
| Total Evaluation | X | ⊙ | ○ | X | ⊙ | ⊙ | ⊙ | ○ |

*[1] Zirconium phosphate
*[2] Homopolymer formed of aromatic sulfonic acid monomer
*[3] Copolymer including styrene sulfonate salt TABLE 1c

|  |  | No. 17 | No. 18 | No. 19 | No. 20 | No. 21 | No. 22 | No. 23 | No. 24 |
|---|---|---|---|---|---|---|---|---|---|
| Attachment amount (g/m$^2$) | Anti-allergen agent A (component a) *[1] | 2.5 | 2.5 | 0.5 | 1.0 | 1.5 | 2.0 | 3.0 | 3.5 |
|  | Anti-allergen agent B (component b) *[2] | 0.3 | 0.3 | 0.06 | 0.12 | 0.18 | 0.24 | 0.36 | 0.42 |
|  | Antiviral agent (component c) *[3] | 0.65 | 0.7 | 0.1 | 0.2 | 0.3 | 0.4 | 0.6 | 0.7 |
|  | Acrylic resin | 0 | 0 | 0 | 0 | 0 | 0 | 0 | 0 |
|  | Polyester resin | 1.1 | 1.1 | 0.22 | 0.44 | 0.66 | 0.88 | 1.32 | 1.54 |
| Anti-allergen property (mite) |  | — | — | 84.8% | 90.0% | 93.8% | 93.8% | 93.8% | 93.8% |
| Anti-allergen property (cedar pollen) |  | — | — | 70.1% | 73.7% | 85.4% | 97.6% | 97.6% | 97.6% |
| Antiviral property (25° C. for 2 hours) |  | — | — | 99.2% (2.1) | 99.9% (3.0) | 99.9% (3.0) | — | — | — |
| Antiviral property (4° C. for 15 minutes) |  | 99.99% (3.9) | 99.99% (4.0) | 91.2% (1.1) | 97.6% (1.6) | 99.7% (2.5) | 99.9% (3.1) | 99.9% (3.2) | 99.9% (3.2) |
| Water spots (grade) |  | 4 | 4 | 4 | 4 | 4 | 4 | 4 | 4 |
| Whitening (grade) |  | 4 | 4 | 4 | 4 | 4 | 4 | 4 | 4 |
| Chalk marks (grade) |  | 4 | 4 | 4 | 4 | 4 | 4 | 3 | 2 |
| Fastness to rubbing DRY (grade) |  | 4.0 | 4.0 | 4.5 | 4.5 | 4.5 | 4.0 | 4.0 | 4.0 |
| Fastness to rubbing WET (grade) |  | 3.5 | 3.5 | 4.0 | 4.0 | 4.0 | 4.0 | 3.5 | 3.5 |
| Flame resistance performance |  | Self-extinguishing | Self-extinguishing | Flame resistance | Flame resistance | Self-extinguishing | Self-extinguishing | 107 (mm/min) | 128 (mm/min) |
| Total Evaluation |  | ○ | ○ | X | ○ | ○ | ⊙ | ○ | X |

*[1] Zirconium phosphate
*[2] Homopolymer formed of aromatic sulfonic acid monomer
*[3] Copolymer including styrene sulfonate salt In the tables, No. 1 shows a blank (unprocessed) fabric. Sample Nos. 2 to 24 show processed fabrics.

No. 2 is a fabric processed with an allergen reduction-processing agent (without an antiviral agent) according to Patent Document 2 (JP 5215424 B2) and is insufficient in the antiviral property.

No. 3 is a fabric processed with a processing agent obtained by adding a copolymer including a styrene sulfonate salt (hereinafter, referred to as an antiviral agent) to the processing agent of No. 2. This processed fabric was confirmed to be likely to generate chalk marks and confirmed to be low in fastness to rubbing in the wet test. No. 4 is a processed fabric obtained by changing the binder of the processing agent in No. 3 from the polyester resin to the acrylic resin. This processed fabric became likely to generate chalk marks as was expected.

Nos. 5 to 8 are fabrics processed with processing agents obtained by reducing in stages zirconium phosphate (hereinafter, referred to as an anti-allergen agent A) from the processing agent in No. 3. It was confirmed that the reduction in the amount of the anti-allergen agent A allows the processed fabric to clear the chalk mark test but does not improve the fastness to rubbing in the wet test.

Nos. 9 to 12 are fabrics processed with processing agents obtained by changing from No. 6 the amount of the homopolymer formed of an aromatic sulfonic acid monomer (hereinafter, referred to as an anti-allergen agent B). No. 10 with 0.3 g/m$^2$ of the anti-allergen agent B was excellent (double circle) in the total evaluation, and No. 11 with 0.2 g/m$^2$ of the anti-allergen agent B was good (circle) in the total evaluation. In contrast, No. 12 with 0.1 g/m$^2$ of the anti-allergen agent B did not satisfy the criteria of the anti-mite and anti-cedar-pollen-allergen properties.

Nos. 13 to 18 are fabrics processed with processing agents obtained by changing the amount of the antiviral agent from No. 10. It was confirmed that even a change in the amount of the antiviral agent to 0.35 to 0.7 can give a good product or an excellent product. Particularly, it was also confirmed that an amount of the antiviral agent of 0.35 to 0.45 can also give higher fastness to rubbing. On the other hand, because it was confirmed from Nos. 10 and 13 to 15 that a change in the amount of the antiviral agent does not almost affect the anti-allergen performance, the anti-allergen property test was not performed for Nos. 16 to 18.

Nos. 19 to 24 are fabrics processed with processing agents obtained by diluting the processing agent used in No. 10 to 20%, 40%, 60%, and 80% or by condensing the processing agent used in No. 10 to 120% and 140%. The processed fabric of No. 19 was confirmed not to satisfy both the criteria of the anti-allergen property and the antiviral property. The processed fabrics of Nos. 20 to 23 cleared all the criteria. The processed fabric of No. 24 was high in the anti-allergy properties and the antiviral property, but was likely to generate chalk marks, thus failing to clear the criterion.

From the test results described above, a fibrous product comprehensively excellent in all the anti-allergen properties, the antiviral property, the water spots, the whitening, the chalk marks, and the fastness to rubbing is considered to be obtained by setting, with respect to the fibrous product, the attachment amount of the anti-allergen agent A to 1.0 to 3.0 g/m$^2$, the attachment amount of the anti-allergen agent B to 0.12 to 0.4 g/m$^2$, and the attachment amount of the antiviral agent to 0.2 to 0.8 g/m$^2$.

Further, the attachment amount of the anti-allergen agent A is more preferably set to 1.5 to 2.5 g/m$^2$, the attachment amount of the anti-allergen agent B to 0.18 to 0.36 g/m$^2$, and the attachment amount of the antiviral agent to 0.3 to 0.7 g/m$^2$, and a comprehensively more excellent fibrous product is considered to be obtained by particularly setting the attachment amount of the anti-allergen agent A to 2.0 to 2.5 g/m$^2$, the attachment amount of the anti-allergen agent B to 0.24 to 0.3 g/m$^2$, and the attachment amount of the antiviral agent to 0.35 to 0.5 g/m$^2$.

Example 2

The processed fabric No. 10 was evaluated in terms of its antiviral property for influenza B (25° C. for 2 hours and 4° C. for 15 minutes). The test method is as follows.

<Antiviral Property (25° C. for 2 Hours)>

A test was performed on the basis of "Determination of antiviral activity of textile products" in ISO18184. Specific procedures are indicated below.
1. A virus suspension (influenza B: ATCC VR-1535) is prepared.
2. With 0.2 mL of the virus suspension is inoculated 0.4 g of the unprocessed fabric (No. 1) or the processed fabric (No. 10).
3. The unprocessed or processed fabric is left to stand at 25° C. for 2 hours, supplied with 20 mL of a washing-out liquid (SCDLP medium), and stirred with a Vortex mixer to wash the virus out of the unprocessed or processed fabric.
4. Host cells (MDCK cells: canine kidney-derived cells) are infected with the virus, and a virus infectivity titer is measured by a plaque assay.
5. An antiviral activity value is calculated, and the fabric having an antiviral activity value of 3 or more is determined to be acceptable.

<Antiviral Property (4° C. for 15 Minutes)>

With an ambient temperature in winter simulated and for confirmation of whether or not the antiviral property can be obtained in a shorter period, a test was performed by changing the conditions for leaving the processed fabric to stand in the procedure "3" from at 25° C. for 2 hours to at 4° C. for 15 minutes. The procedures other than the conditions for leaving the fabric to stand are as mentioned above.

The fabric having an antiviral activity value of 3 or more is determined to be acceptable.

The test results are indicated below.

TABLE 2

| | Antiviral property for influenza B | | | |
|---|---|---|---|---|
| Sample | Virus infectivity titer (PFU/vial)*[1] Common logarithmic average value | | Decrease value [M]*[2] | Antiviral activity value [Mv]*[3] |
| (1) 25° C. for 2 hours | | | | |
| Standard fabric (cotton unprocessed fabric) | Immediately after inoculation [Ig(Va)] Left to stand for 2 hours [Ig(Vb)] | 7.49 7.07 | 0.4 | — |
| Unprocessed fabric (No. 1) | Left to stand for 2 hours [Ig(Vc)] | 7.35 | — | −0.3 |
| Processed fabric (No. 10) | Left to stand for 2 hours [Ig(Vc)] | <2.30 | — | ≥4.8 |
| (2) 4° C. for 15 minutes | | | | |
| Standard fabric (cotton unprocessed fabric) | Immediately after inoculations [Ig(Va)] Left to stand for 15 minutes [Ig(Vb)] | 7.49 7.39 | 0.1 | — |
| Unprocessed fabric (No. 1) | Left to stand for 15 minutes [Ig(Vc)] | 7.59 | — | −0.2 |
| Processed fabric (No. 10) | Left to stand for 15 minutes [Ig(Vc)] | <2.30 | — | ≥5.1 |

*[1]PFU = plaque forming units
*[2]Decrease value [M] = Ig(Va) − Ig(Vb) (required value for test validity: decrease value [M] ≤2.0)
*[3]Antiviral activity value [Mv] = Ig(Vb) − Ig(Vc)

As shown in Table 2, an antiviral effect was not observed in the unprocessed fabric (No. 1), whereas the processed fabric (No. 10) exhibited a high antiviral activity value in both at 25° C. for 2 hours and at 4° C. for 15 minutes.

Accordingly, the results of Examples 1 and 2 demonstrated that the fibrous product according to the present invention exhibits high antiviral action for both influenza viruses A and B.

Example 3

Antibacterial Test

The processed fabric No. 22 was evaluated for its antibacterial performance. As bacterial bodies, *Escherichia coli* (NBRC 3301) and *Staphylococcus aureus* (NBRC 12732) were used.

Measurement is performed in accordance with JIS L1902 (Bacterial Liquid Absorption Method), and the fabric is determined to be acceptable when having a bacteriostatic activity value of 2.0 or more and a bactericidal activity value of 0 or more.

Table 3 shows the results.

TABLE 3

| Sample | Common logarithmic average value of number of live bacteria | | Bacteriostatic activity value [S]*[1] | Bactericidal activity value [L]*[2] |
|---|---|---|---|---|
| *(1) Escherichia coli* | | | | |
| Standard fabric (cotton unprocessed fabric) | Immediately after inoculation [Ma] | 4.5 | — | — |
| | After cultivation for 18 hours [Mb] | 7.5 | | |
| Processed fabric (No. 22) | Immediately after inoculation [Mo] | 4.2 | >5.9 | >3.2 |
| | After cultivation for 18 hours [Mc] | <1.3 | | |
| *(2) Staphylococcus aureus* | | | | |
| Standard fabric (cotton unprocessed fabric) | Immediately after inoculation [Ma] | 4.5 | — | — |
| | After cultivation for 18 hours [Mb] | 7.1 | | |
| Processed fabric (No. 22) | Immediately after inoculation [Mo] | 4.0 | >5.4 | >3.2 |
| | After cultivation for 18 hours [Mc] | <1.3 | | |

*[1]Bacteriostatic activity value [S] = (Mb − Ma) − (Mc − Mo)
*[2]Bactericidal activity value [L] = Ma − Mc As shown in Table 3, the processed fabric No. 22 exhibited excellent antibacterial activity for both *Escherichia coli* and *Staphylococcus aureus* and cleared the criteria for acceptance.

This result demonstrated that the fibrous product of the present invention has antibacterial activity as well as antiviral activity. This antibacterial activity is considered to be a result of contribution of the anti-allergen agent A (zirconium phosphate).

INDUSTRIAL APPLICABILITY

A fibrous product processed with a processing agent of the present invention has excellent anti-allergen and antiviral properties. The fibrous product is less likely to generate water spots, whitening, chalk marks, and color migration, so that it is suitable for use as an interior material for, for example, an airplane and a vehicle, and interior accessories such as furniture, a curtain, a mat, and synthetic leather.

The invention claimed is:

1. A fibrous product having, attached thereto
   (a) 1.0 to 3.0 g/m$^2$ of zirconium phosphate;
   (b) 0.12 to 0.4 g/m$^2$ of a homopolymer formed of an aromatic sulfonic acid monomer; and
   (c) 0.2 to 0.8 g/m$^2$ of a copolymer including a styrene sulfonate salt.

2. The fibrous product according to claim 1, wherein
   an attachment amount of the zirconium phosphate (a) is 1.5 to 2.5 g/m$^2$,
   an attachment amount of the homopolymer (b) formed of an aromatic sulfonic acid monomer is 0.18 to 0.36 g/m$^2$, and
   an attachment amount of the copolymer (c) including a styrene sulfonate salt is 0.3 to 0.7 g/m$^2$.

3. The fibrous product according to claim 1, wherein
   an attachment amount of the zirconium phosphate (a) is 2.0 to 2.5 g/m$^2$,
   an attachment amount of the homopolymer (b) formed of an aromatic sulfonic acid monomer is 0.24 to 0.3 g/m$^2$, and
   an attachment amount of the copolymer (c) including a styrene sulfonate salt is 0.35 to 0.5 g/m$^2$.

4. The fibrous product according to claim 1, wherein the components (a) to (c) are attached to the fibrous product with a hinder, and an attachment amount of the binder is 0.05 to 1.5 g/m$^2$.

5. The fibrous product according to claim 4, wherein the binder is a polyester resin.

6. The fibrous product according to claim 1, wherein the fibrous product has an anti-allergen property and an antiviral property.

7. A processing agent for producing the fibrous product according to claim 1, the processing agent being an aqueous dispersion that contains the zirconium phosphate (a), the homopolymer (b) formed of an aromatic sulfonic acid monomer, and the copolymer (c) including a styrene sulfonate salt in a weight ratio of 1.0 to 3.0:0.12 to 0.4:0.2 to 0.8.

* * * * *